United States Patent
Robl et al.

(10) Patent No.: US 7,358,254 B2
(45) Date of Patent: Apr. 15, 2008

(54) METHOD FOR TREATING ATHEROSCLEROSIS EMPLOYING AN AP2 INHIBITOR AND COMBINATION

(75) Inventors: Jeffrey A. Robl, Newtown, PA (US); Rex A. Parker, Titusville, NJ (US); Scott A. Biller, Lexington, MA (US); Haris Jamil, Libertyville, IL (US); Bruce L. Jacobson, Carlsbad, CA (US); Krishna Kodukula, Princeton, NJ (US); Gokhan Hotamisligil, Wellesley, MA (US)

(73) Assignees: Bristol-Myers Squibb Company, Princeton, NJ (US); President & Fellows of Harvard College, Cambridge, MA (US)

( * ) Notice: Subject to any disclaimer, the term of this patent is extended or adjusted under 35 U.S.C. 154(b) by 214 days.

(21) Appl. No.: 10/872,721

(22) Filed: Jun. 21, 2004

(65) Prior Publication Data

US 2004/0229807 A1    Nov. 18, 2004

(51) Int. Cl.
*A61K 31/505* (2006.01)
*A61K 38/00* (2006.01)
*C07D 275/06* (2006.01)
*C07D 413/00* (2006.01)

(52) U.S. Cl. .......... 514/256; 514/12; 514/374; 548/210; 548/232; 548/235; 548/236; 530/324

(58) Field of Classification Search .......... 514/256, 514/12, 374; 548/210, 232, 235, 236; 530/324
See application file for complete search history.

(56) References Cited

U.S. PATENT DOCUMENTS

| 4,001,228 | A |   | 1/1977  | Mattalia ............. 260/247.1 M |
|-----------|---|---|---------|------------------------------------|
| 4,051,250 | A |   | 9/1977  | Dahm et al. .......... 424/272 |
| 5,187,188 | A |   | 2/1993  | Meanwell ............. 514/374 |
| 5,218,124 | A |   | 6/1993  | Failli et al. .......... 548/180 |
| 5,254,576 | A |   | 10/1993 | Romine et al. ........ 514/365 |
| 5,262,540 | A |   | 11/1993 | Meanwell ............. 514/374 |
| 5,348,969 | A |   | 9/1994  | Romine et al. ........ 514/376 |
| 5,362,879 | A |   | 11/1994 | Meanwell ............. 548/236 |
| 5,380,854 | A |   | 1/1995  | Romine et al. ........ 548/235 |
| 5,403,852 | A |   | 4/1995  | Barreau et al. ........ 514/374 |
| 5,599,770 | A |   | 2/1997  | Kubota et al. ......... 504/242 |
| 5,612,359 | A | * | 3/1997  | Murugesan ............ 514/365 |

FOREIGN PATENT DOCUMENTS

| FR | 2.1.56.486   | 1/1973  |
|----|--------------|---------|
| FR | 2.647.676    | 7/1990  |
| RU | 2054936      | 4/1994  |
| SU | 2033184      | 6/1990  |
| WO | WO92/04334   | 3/1992  |
| WO | WO95/17393   | 6/1995  |
| WO | WO/96/35678  | 11/1996 |

OTHER PUBLICATIONS

Kletzien et al., J.Cel.Biochem.Suppl., vol. 15, No. 8, p. 70 (XP002209109) (1991).
Melki et al., J. Lipid Res., vol. 34, No. 9, pp. 1527-1534 (XP001094445) (1993).
Baxa, et al. Biochemistry, vol. 28, No. 22, 1989 pp. 8683-8690.
Hotamisligil, G.S. et al, "Uncoupling of Obesity from Insulin Resistance Through a Targeted Mutation in aP2, the Adipocyte Fatty Acid Binding Protein", Science, Vo. 274, Nov. 22, 1996, pp. 1377-1379.
Mai, A. et al, "Dihydro(alkylthio)(naphthylmethyl)oxopyrimidines: Novel Non-Nucleoside Reverse Transcriptase Inhibitors of the S-DABO Series", J. Med. Chem., 1997, 40, 1447-1454.
Dialog Alert DBDR928, Jan. 2, 1997, Pharmaprojects No. 5149.

* cited by examiner

*Primary Examiner*—Jon Weber
*Assistant Examiner*—Abdel A Mohamed
(74) *Attorney, Agent, or Firm*—Rosemary M. Miano; Joseph C. Wang; Laurelee A. Duncan

(57) ABSTRACT

A method is provided for treating atherosclerosis and related diseases, employing an aP2 inhibitor or a combination of an aP2 inhibitor and another antiatherosclerotic agent, for example, an HMG CoA reductase inhibitor such as pravastatin.

2 Claims, 1 Drawing Sheet

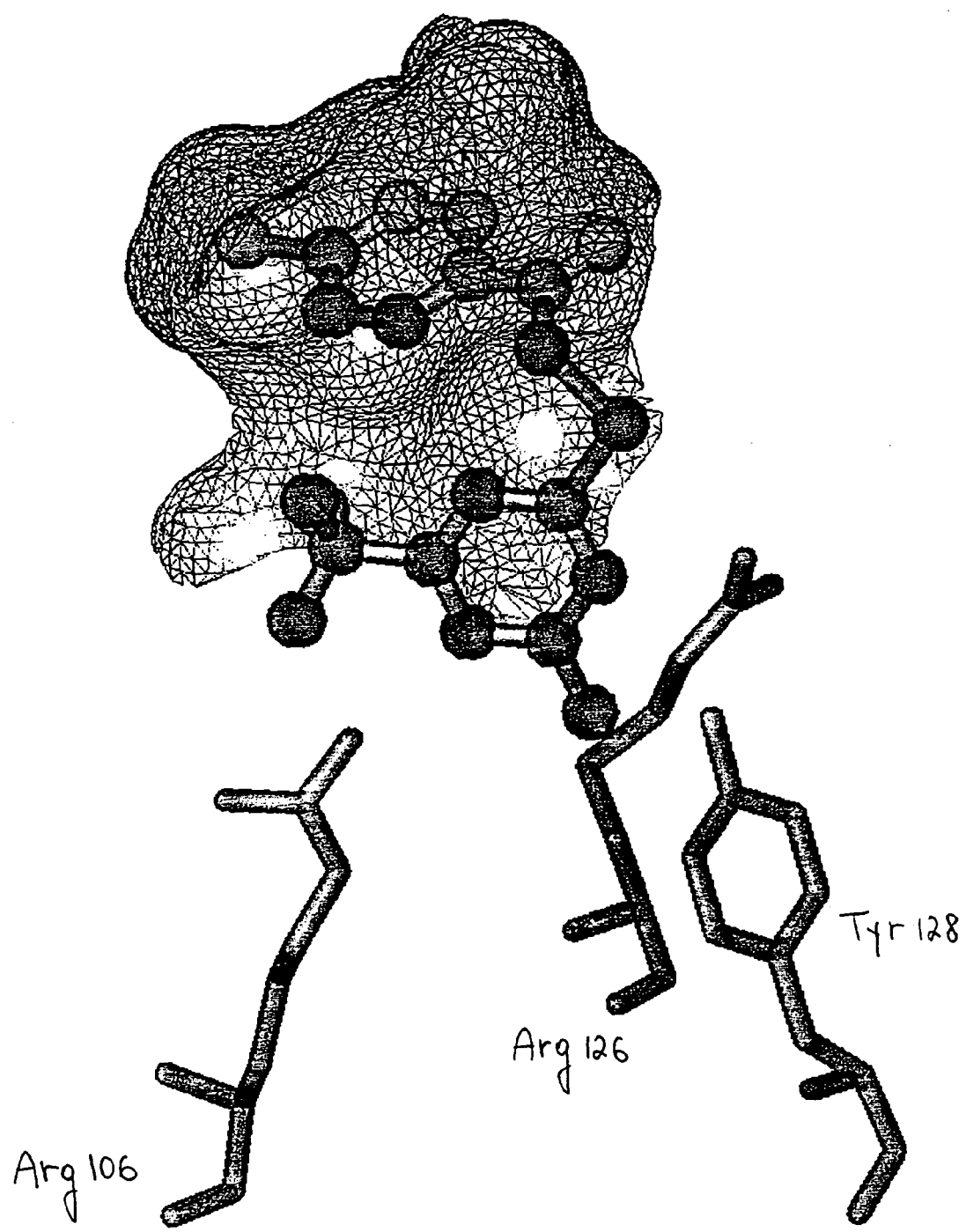
FIGURE

```
                    SEQUENCE LISTING

<160> NUMBER OF SEQ ID NOS: 1

<210> SEQ ID NO 1
<211> LENGTH: 132
<212> TYPE: PRT
<213> ORGANISM: HOMO SAPIENS

<400> SEQUENCE: 1

Met Cys Asp Ala Phe Val Gly Thr Trp Lys Leu Val Ser Ser Glu Asn
1               5                   10                  15

Phe Asp Asp Tyr Met Lys Glu Val Gly Val Gly Phe Ala Thr Arg Lys
                20                  25                  30

Val Ala Gly Met Ala Lys Pro Asn Met Ile Ile Ser Val Asn Gly Asp
            35                  40                  45

Val Ile Thr Ile Lys Ser Glu Ser Thr Phe Lys Asn Thr Glu Ile Ser
        50                  55                  60

Phe Ile Leu Gly Gln Glu Phe Asp Glu Val Thr Ala Asp Asp Arg Lys
65                  70                  75                  80

Val Lys Ser Thr Ile Thr Leu Asp Gly Gly Val Leu Val His Val Gln
                85                  90                  95

Lys Trp Asp Gly Lys Ser Thr Thr Ile Lys Arg Lys Arg Glu Asp Asp
                100                 105                 110

Lys Leu Val Val Glu Cys Val Met Lys Gly Val Thr Ser Thr Arg Val
            115                 120                 125

Tyr Glu Arg Ala
            130
```

METHOD FOR TREATING ATHEROSCLEROSIS EMPLOYING AN AP2 INHIBITOR AND COMBINATION

FIELD OF THE INVENTION

The present invention relates to a method for treating atherosclerosis and related diseases, employing an aP2 inhibitor alone or in combination with another type antiatherosclerotic agent.

BACKGROUND OF THE INVENTION

Fatty acid binding proteins (FABPs) are small cytoplasmic proteins which bind to fatty acids such as oleic acids which are important metabolic fuels and cellular regulators. Dysregulation of fatty acid metabolism in adipose tissue is a prominent feature of insulin resistance and the transition from obesity to non-insulin dependent diabetes mellitus (NIDDM or Type II diabetes).

aP2, an abundant 14.6 KDa cytosolic protein in adipocytes, and one of a family of homologous intracellular fatty acid binding proteins (FABPs), is involved in the regulation of fatty acid trafficking in adipocytes and mediates fatty acid fluxes in adipose tissue. G. S. Hotamisligil et al, "Uncoupling of Obesity from Insulin Resistance Through a Targeted Mutation in aP2, the Adipocyte Fatty Acid Binding Protein", Science, Vol. 274, Nov. 22, 1996, pp. 1377-1379, report that aP2-deficient mice placed on a high fat diet for several weeks developed dietary obesity, but, unlike control-mice on a similar diet, did not develop insulin resistance or diabetes. Hotamisligil et al conclude that "aP2 is central to the pathway that links obesity to insulin resistance" (Abstract, page 1377).

DIALOG ALERT DBDR928 dates Jan. 2, 1997, Pharmaprojects No. 5149 (Knight-Ridder Information) discloses that a major drug company "is using virtual screening techniques to identify potential new antidiabetic compounds." It is reported that "the company is screening using aP2, a protein related to adipocyte fatty acid binding protein."

DESCRIPTION OF THE INVENTION

In accordance with the present invention, a method is provided for treating atherosclerosis wherein a therapeutically effective amount of a drug which inhibits aP2 (aP2 inhibitor) is administered to a human patient in need of treatment.

In addition, in accordance with the present invention, a method is provided for treating atherosclerosis, wherein a therapeutically effective amount of a combination of an aP2 inhibitor and another type of antiatherosclerotic agent is administered to a human patient in need of treatment.

Furthermore, in accordance with the present invention, a novel antiatherosclerotic combination is provided which is formed of a drug which inhibits aP2 and an antiatherosclerotic agent which functions by a mechanism other than by inhibiting aP2. The aP2 inhibitor will be employed in a weight ratio to the antiatherosclerotic agent (depending upon its mode of operation) within the range from about 0.01:1 to about 100:1, preferably from about 0.5:1 to about 10:1.

It will be appreciated that the method of the invention for treating atherosclerosis employing an aP2 inhibitor alone or in combination with an antiatherosclerotic agent encompasses treating, reducing risk of, inhibiting, preventing and/or reducing or causing regression of atherosclerosis.

The method of the invention also encompasses preventing, inhibiting or reducing risk of cardiovascular and cerebrovasculer diseases resulting from atherosclerosis, such as cardiac and/or cerebral ischemia, myocardial infarction, angina, peripheral vascular disease and stroke.

The aP2 inhibitors suitable for use in the method of the invention are compounds which bind to the aP2 protein and inhibits its function and/or its ability to bind free fatty acids. The compounds will preferably contain less than 60 carbon atoms, more preferably less than 45 carbon atoms, and will contain less than 20 heteroatoms, more preferably less than 12 heteroatoms. They contain a hydrogen bond donator or acceptor group, preferably acidic in nature, which includes, but is not limited to, $CO_2H$, tetrazole, $SO_3H$, $PO_3H$, $P(R)(O)OH$ (where R is lower alkyl or lower alkoxy), OH, $NHSO_2R'$ or $CONHSO_2R'$ (where R' is lower alkyl), and thiazolidindione, and interacts (directly or through an intervening water molecule), either by ionic or hydrogen bonding interactions, with one, two, or three of the three amino acid residues, designated as Arg 106, Arg 126 and Tyr 128 in human aP2, within the aP2 protein.

The compounds suitable for use herein preferably contain an additional substituent, preferably hydrophobic in nature, which include the following groups: alkyl, cycloalkyl, aryl, heteroaryl, cycloheteroalkyl, benzo-fused aryl and heteroaryl, and their substituted counterparts. Especially preferred are aryl and substituted aryl groups. More especially preferred is phenyl and halo or methyl substituted phenyl.

The hydrophobic substituent binds to (in) and/or interacts with a discrete pocket within the aP2 protein defined roughly by the amino acid residues Phe 16, Tyr 19, Met 20, Val 23, Val 25, Ala 33, Phe 57, Thr 74, Ala 75, Asp 76, Arg 78 in human aP2. The through space distance from the hydrogen bond donor/acceptor group and the additional substituent group is within the distance of about 7 to about 15 Angstroms.

The above compounds may be employed in the form of pharmaceutically acceptable salts thereof and prodrug esters thereof.

The term "antiatherosclerotic agent" as employed herein refers to antihyperlipidemic agents including HMG CoA reductase inhibitors, microsomal triglyceride transfer protein (MTP) inhibitors, fibric acid derivatives, squalene synthetase inhibitors and other known cholesterol lowering agents, lipoxygenase inhibitors, ACAT inhibitors, and PPAR α/γ dual agonists as disclosed hereinafter.

BRIEF DESCRIPTION OF FIGURE

The accompanying FIGURE is a computer generated image of a partial X-ray structure of compound XVIA (described hereinafter) bound to human aP2.

DETAILED DESCRIPTION OF THE INVENTION

Examples of aP2 inhibitors suitable for use herein include compounds which include an oxazole or analogous ring. Thus, U.S. Pat. No. 5,218,124 to Failli et al (the disclosure of which is incorporated herein by reference) discloses compounds, which have activity as aP2 inhibitors and thus suitable for use herein, which include substituted benzoylbenzene, bipheny- and 2-oxazole-alkanoic acid derivatives having the following structure:

$$A(CH_2)_nO—B \qquad I$$

wherein
A is a group having the formula

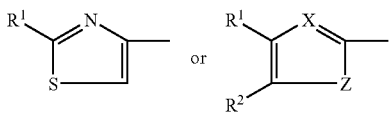

wherein
X is —N— or

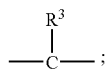

Z is

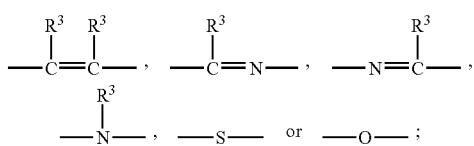

$R^1$ is hydrogen, lower alkyl or phenyl;
$R^2$ is hydrogen or lower alkyl; or
$R^1$ and $R^2$ taken together form a benzene ring, with the proviso that when X is —N—, Z is other than

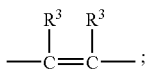

$R^3$ is hydrogen or lower alkyl;
n is 1-2;
B is

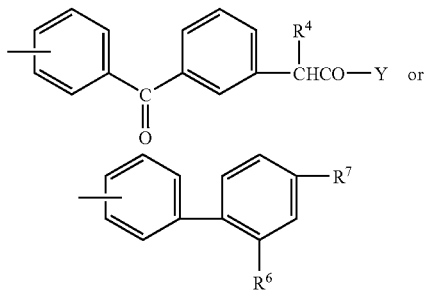

wherein
Y is $OR^5$ or $N(OH)R^8$;
$R^4$ and $R^5$ are each, independently, hydrogen or lower alkyl;
$R^6$ is hydrogen, halo or nitro;
$R^7$ is

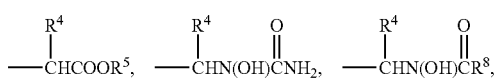

-continued

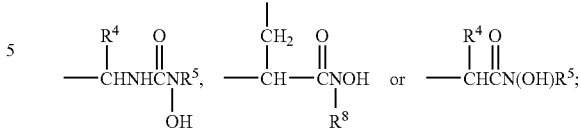

$R^8$ is lower alkyl;
m is 0-3;

and the pharmacologically acceptable salts thereof.

The grouping A embraces, inter alia, 5- or 6-membered unsaturated nitrogen, sulfur or oxygen containing mono- or benzofused-heterocycles, optionally substituted with lower alkyl or phenyl. The foregoing definition embraces the following heterocyclic moieties; furyl, pyrrolyl, thienyl, oxazolyl, thiazolyl, imidazolyl, pyridyl, pyrazinyl, pyrimidinyl, benzofuranyl, benzothienyl, benzothiazolyl, indolyl, benzoxazolyl, quinazolinyl, benzimidazolyl, quinoxalinyl, quinazolinyl and the like.

Preferred are the examples where A is defined as above and B is and $R^7$ is

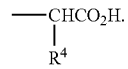

In another embodiment of the present invention, compounds which have activity as aP2 inhibitors suitable for use herein are disclosed in U.S. Pat. No. 5,403,852 to Barreau et al (which is incorporated herein by reference) which are oxazole derivatives and have the structure

II

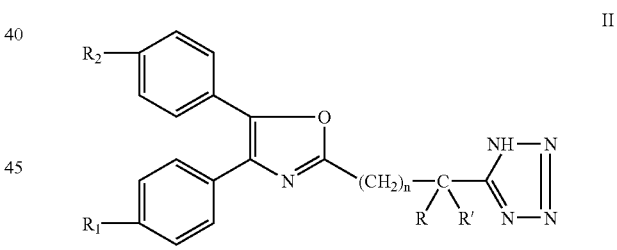

in which;
R and R' are identical or different and represent a hydrogen atom or an alkyl radical containing 1 or 2 carbon atoms,
$R_1$ and $R_2$ are identical or different and represent hydrogen or halogen atoms or alkyloxy radicals in which the alkyl portion contains 1 to 4 carbon atoms in a straight or branched chain, and
n equals 3 to 6,
as well to their salts, to their isomers where they exist and to pharmaceutical compositions containing them.

In addition, other compounds which have activity as aP2 inhibitors suitable for use in the method of the invention are compounds disclosed in U.S. Pat. No. 4,001,228 to Mattalia (which is incorporated herein by reference) which are 2-thiol-4,5-diphenyloxazole S-derivatives which have the structure

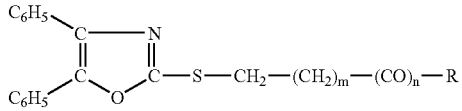

III wherein m is 0, 1 or 2, n is 1 and R represents hydroxy, alkoxy or amino. Also included within the scope of this invention are salts of the compounds of formula III above, particularly pharmaceutically acceptable addition salts thereof.

Preferred are S-(4,5-diphenyloxazol-2-yl)-mercaptocarboxylic acids of the formula:

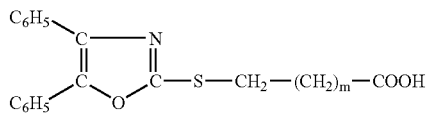

wherein m is 0, 1 or 2, and pharmaceutically acceptable lower alkyl esters and salts thereof.

In another embodiment of the present invention, compounds which have activity as aP2 inhibitors suitable for use herein are disclosed in U.S. Pat. No. 4,051,250 to Dahm et al (the disclosure of which is incorporated herein by reference) which discloses azole derivatives of the structure

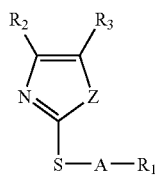

IV wherein $R_1$ is carboxyl, esterified carboxyl or other functionally modified carboxyl group; $R_2$ and $R_3$ each are aryl of up to 10 carbon atoms; A is $C_nH_{2n}$ in which n is an integer from 1 to 10, inclusive; and Z is O or S, and the physiologically acceptable salts thereof.

Preferred are preferred compounds as disclosed in the Dahm et al patent.

In still another embodiment of the invention, compounds which have activity as aP2 inhibitors suitable for use herein are disclosed in U.S. Pat. No. 5,380,854 to Romine et al (the disclosure of which is incorporated herein by reference) and are phenyl-heterocyclic oxazole derivatives which have the structure

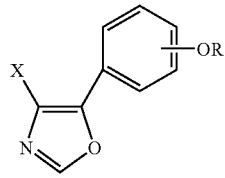

V

-continued

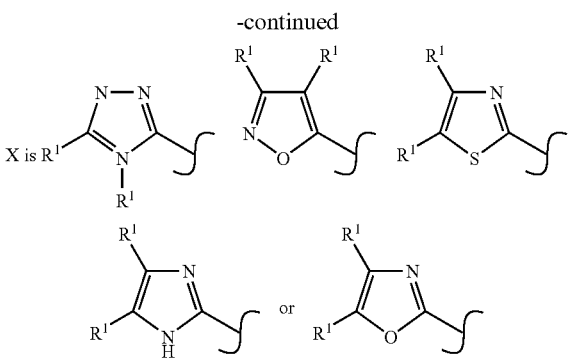

R is $CH_2R^2$;
$R^1$ is Ph or Th;
$R^2$ is

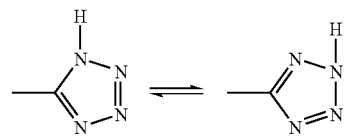

$CO_2R^3$, and
$R^3$ is H, or $C_1$-$C_4$ lower alkyl;

or pharmaceutically acceptable salt thereof.

Preferred are the compounds where R is $CH_2CO_2H$ and

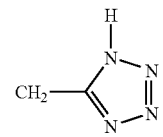

or its tautomer and $R^1$ is Ph.

In yet another embodiment of the method of the invention, compounds which have activity as aP2 inhibitors suitable for use herein are disclosed in PCT application WO 95/17393 which are diaryloxazole derivatives having the structure

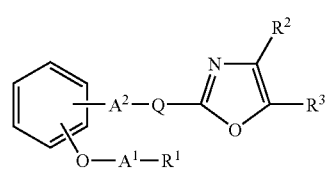

VI wherein $R^1$ is carboxy or protected carboxy,
$R^2$ is aryl which may have suitable substituent(s),
$R^3$ is aryl which may have suitable substituent(s),
$A^1$ is lower alkylene,
$A^2$ is bond or lower alkylene and
-Q- is

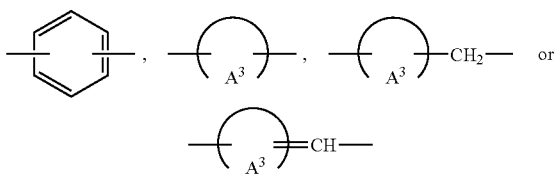

(in which

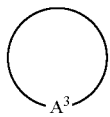

is cyclo (lower)alkane or cycle(lower)alkene, each of which may have suitable substituent(s)).

Preferred are the preferred compounds of WO 95/17393 as illustrated by the working Examples thereof.

Another embodiment of compounds which have activity as aP2 inhibitors suitable for use herein are disclosed in U.S. Pat. No. 5,362,879 to Meanwell (the disclosure of which is incorporated herein by reference) which are 4,5-diphenyloxazole derivatives having the structures

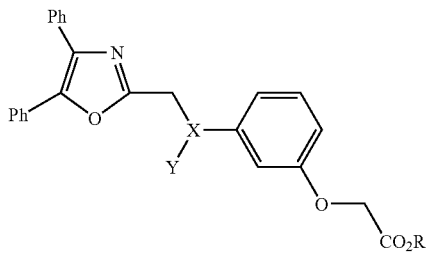

VIIA wherein
R is H or $C_1$-$C_5$ lower alkyl,
X is N or CH,
Y is H or $CO_2R^1$, or $COR^2$,
$R^1$ is $C_1$-$C_5$ lower alkyl, or phenylmethyl, and
$R^2$ is $C_1$-$C_5$ alkyl;

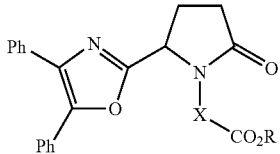

VIIB wherein
R is H or $C_1$-$C_5$ lower alkyl,
X is $(CH_2)_n$ or para or meta substituted phenyl
wherein the substituent is $OR^2$,
$R^2$ is $C_1$-$C_5$ alkyl, and
n is an integer of 4 to 8, and pharmaceutically acceptable salts thereof.

Preferred are the preferred compounds of the Meanwell patent as illustrated by the working Examples thereof.

In still another embodiment of the present invention, compounds which have activity as aP2 inhibitors suitable for use herein are disclosed in U.S. Pat. No. 5,187,188 to Meanwell (the disclosure of which is incorporated herein by reference) which are oxazole carboxylic acid derivatives having the structure

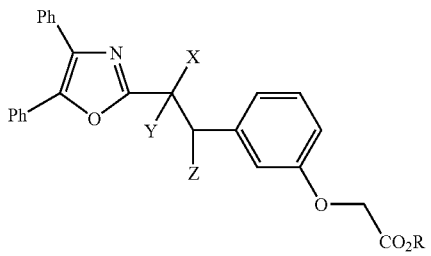

VIII wherein
Y and Z are independently hydrogen or together form a bond;
X is CN, $CO_2R^1$ or $CONR^2R^3$;
R and $R^1$ are independently or together H, Na, or $C_1$-$C_5$ lower alkyl;
$R^2$ and $R^3$ are independently or together H, or $C_1$-$C_5$ lower alkyl;
or alkali metal salt thereof.

Preferred are the preferred compounds of the above Meanwell patent as illustrated by the working Examples thereof.

In another embodiment of the invention, compounds which have activity as aP2 inhibitors suitable for use herein are disclosed in U.S. Pat. No. 5,348,969 to Romine et al (the disclosure of which is incorporated herein by reference) which are phenyloxazolyloxazole derivatives having the structure

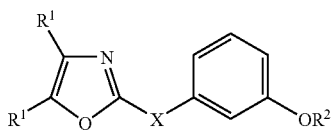

IX wherein
x is

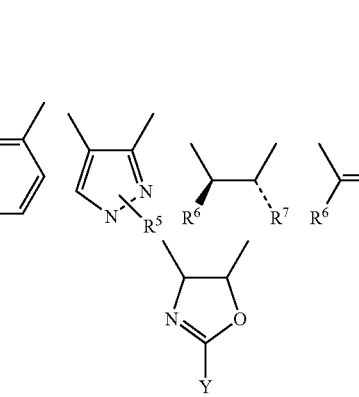

Y is $C_3$, Ph, or OH, provided that when Y is OH, the compound exists an the kero-enol tautaumerism form

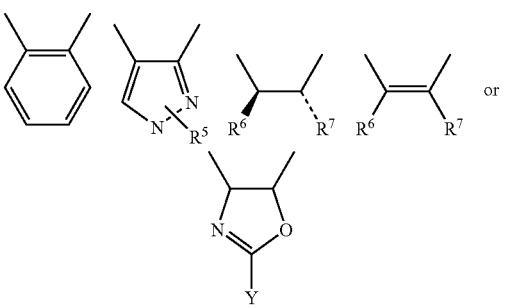

$R^1$ is Ph or Th;
$R^2$ is $CH_2R^3$;

$R^3$ is $CO_2R^4$;
$R^4$ is H or $C_1$-$C_5$ lower alkyl;
$R^5$ is H or $CH_3$; $R^6$ is OHCHN or $H_2N$; and
$R^7$ is H or OH;

or pharmaceutically acceptable salt thereof.

Preferred are the preferred compounds as delineated in the Romine et al patent and in the working Examples thereof, especially where X is

and $R^2$ is $CH_2CO_2H$.

In addition, compounds which have activity as aP2 inhibitors which may be employed herein include those disclosed in U.S. Pat. No. 5,262,540 to Meanwell (the disclosure of which is incorporated herein by reference) and are 2-(4,5-diaryl)-2-oxazolyl substituted phenoxyalkanoic acids and esters having the structure

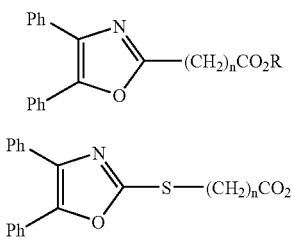

XA

XB (wherein n is 7-9 and R is hydrogen or lower alkyl; or when R is hydrogen, the alkali metal salt thereof),

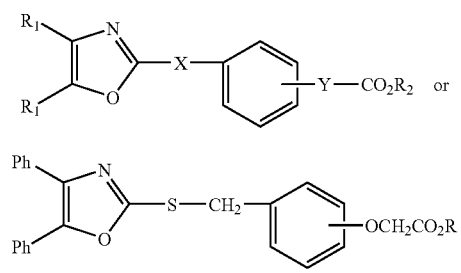

XC

XD wherein
$R_1$ is phenyl or thienyl;
$R_2$ is hydrogen, lower alkyl or together with $CO_2$ is tetrazol-1-yl;
X is a divalent connecting group selected from the group consisting of $CH_2CH_2$, CH=CH, and $CH_2O$;
Y is a divalent connecting group attached to the 3- or 4-phenyl position selected from the group consisting of $OCH_2$, $CH_2CH_2$ and CH=CH,
or when $R_2$ is hydrogen, an alkali metal salt thereof.

Preferred are the preferred compounds as set out in the above Meanwell et al patent as illustrated in the working Examples thereof.

In another embodiment of the invention, compounds which have activity as aP2 inhibitors suitable for use herein are disclosed in PCT application WO 92/04334 which are substituted 4,5-diaryl heterocycles having the formula

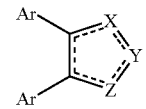

XI in which
each group Ar is the same or different and is optionally substituted phenyl or optionally substituted heteroaryl;
X is nitrogen or $CR^1$;
Y is nitrogen, $N(CH_2)_nA$ or $C(CH_2)_nA$;
Z is nitrogen, oxygen or $N(CH_2)_nA$, and the dotted line indicates the optional presence of a double bond so as to form a fully unsaturated heterocyclic ring;
$R^1$ is hydrogen, $C_{1-4}$alkyl, optionally substituted phenyl or optionally substituted heteroaryl;
n is 4 to 12; and
A is $CO_2H$ or a group hydrolysable to $CO_2H$, 5-tetrazolyl, $SO_3H$, $P(O)(OR)_2$, $P(O)(OH)_2$, or $P(O)(R)(OR)$ in which R is hydrogen or $C_{1-4}$alkyl, or a pharmaceutically acceptable salt thereof.

Preferred are preferred compounds of WO 92/04334.

In yet another embodiment of the invention, compounds which have activity as aP2 inhibitors suitable for use herein are disclosed in French Patent 2156486 which have the structure

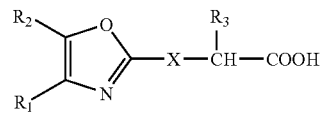

XII

Where X is O or S;
$R_1$ is H, phenyl or phenyl substituted with F, Cl or Br or alkoxy,
$R_2$ is H, alkyl, phenyl or phenyl substituted with F, Cl or Br or alkoxy, and
$R_3$ is H or alkyl.

Preferred are those preferred compounds as set out in French Patent No. 2156486.

Most preferred oxazole compounds as aP2 inhibitors are the compounds

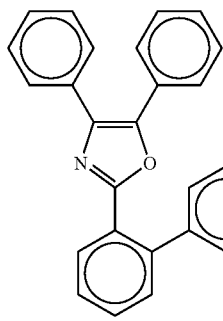

and

-continued

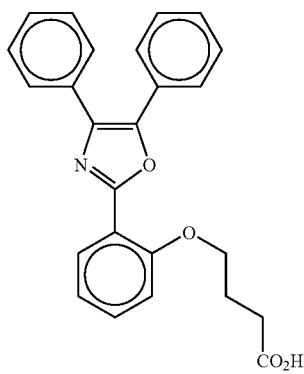

which may be prepared as disclosed in U.S. Pat. No. 5,348,969 to Romine et al.

Another class of aP2 inhibitors suitable for use in the method of the invention include pyrimidine derivatives. Thus, U.S. Pat. No. 5,599,770 to Kubota et al (the disclosure of which is incorporated herein by reference) disclose compounds which have activity as aP2 inhibitors and thus suitable for use herein include 2-benzyloxypyrimidine derivatives having the following structure

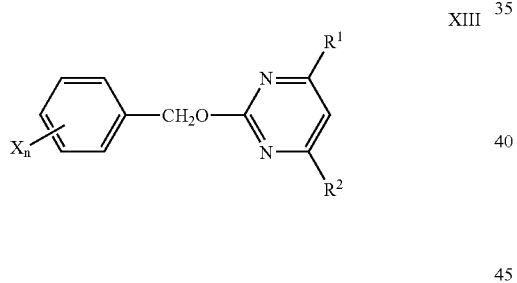

XIII wherein $R^1$ and $R^2$ are each independently H, a halogen, hydroxyl, $C_1$-$C_4$ alkyl, $C_1$-$C_4$ haloalkyl, $C_3$-$C_5$ alkenyl, $C_3$-$C_5$ alkynyl, $C_1$-$C_4$ alkoxy, $C_1$-$C_4$ haloalkoxy, $C_3$-$C_5$ alkenyloxy, $C_3$-$C_5$ alkynyloxy, $C_1$-$C_4$ alkylthio, or phenyl, with the proviso that at least one of $R^1$ and $R^2$ must be hydroxyl;

n is an integer of 0 to 5; and each X which may be identical or different if n is greater than 1, is a halogen, $C_1$-$C_4$ alkyl, $C_1$-$C_4$ haloalkyl, $C_1$-$C_4$ alkoxy, $C_1$-$C_4$ alkylthio, $C_7$-$C_9$ aralkyloxy, phenyl, hydroxymethyl, hydroxycarbonyl, $C_1$-$C_4$ alkoxycarbonyl, or nitro.

Preferred are the compounds in which either $R^1$ or $R^2$ is hydroxyl and the other $R^1$ or $R^2$ is $C_1$-$C_4$ alkyl and X is halogen.

In another embodiment of the method of the invention, compounds which have activity as aP2 inhibitors suitable for use herein are disclosed in A. Mai et al "Dihydro(alkylthio)-(naphthylmethyl)oxopyrimidines: Novel Non-Nucleoside Reverse Transcriptase Inhibitors of the S-DABO. Series", J. Med. Chem., 1997, 40, 1447-1454 which have the structures

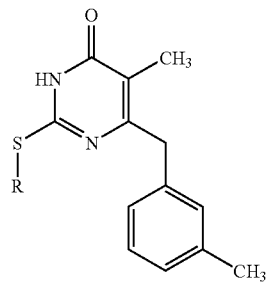

XIVA

3a R = sec-butyl
3b R = cyclopentyl
3c R = cyclohexyl

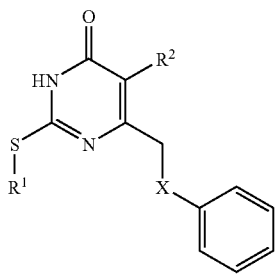

XIVB

5 X = CH$_2$
6 X = O
7 X = S

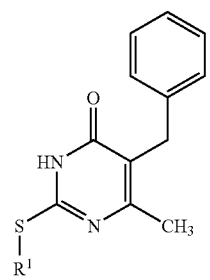

XIVC

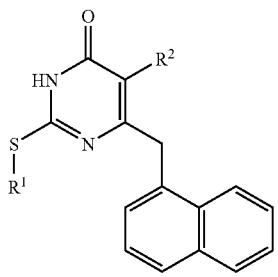

XIVD

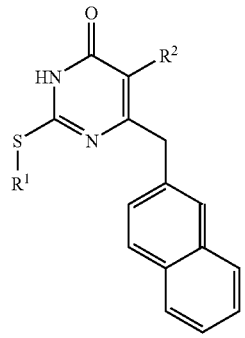

XIVE $R^1$ = sec-butyl, cyclopentyl, cyclohexyl;

$R^2$ = H, $CH_3$. The structures XIVA-XIVE are depicted in their keto form. However, it will be apparent to one skilled in the art that they may also exist in their enol form to give structures of the type

XIVF

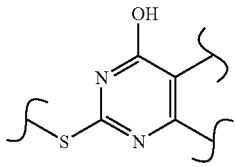

In yet another embodiment of the method of the invention, compounds which have activity as aP2 inhibitors suitable for use herein are disclosed in PCT application WO 96/35678 which are α-substituted pyrimidine-thioalkyl and alkylether compounds which have the structure

XVI

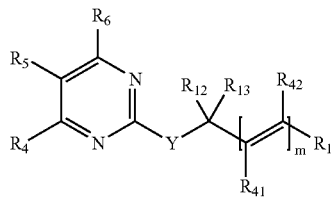

where m is 0 or 1;
$R^1$ is selected from —$CO_2R_{53}$, —$CONR_{54}R_{55}$,

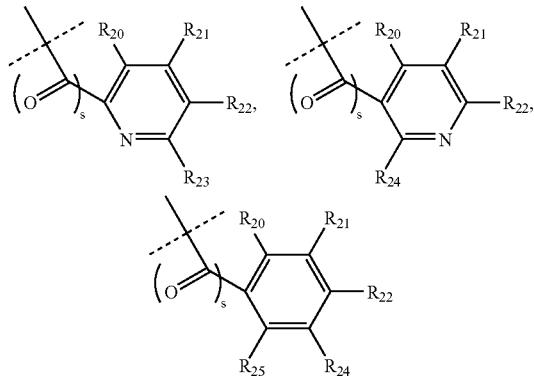

where s is 0 or 1, and $R_{20}$, $R_{21}$, $R_{22}$, $R_{23}$, $R_{24}$, and $R_{25}$ are the same or different and are selected from —H, $C_1$-$C_6$ alkyl, $C_1$-$C_6$ alkenyl, $C_1$-$C_6$ alkoxy, $C_1$-$C_6$ alkylthio, $C_3$-$C_8$ cycloalkyl, —$CF_3$, —$NO_2$, -halo, —OH, —CN, phenyl, phenylthio, -styryl, —$CO_2(R_{31})$, —$CON(R_{31})(R_{32})$, —CO ($R_{31}$), —$(CH_2)_n$—$N(R_{31})(R_{32})$, —C(OH) ($R_{31})(R_{33})$, —$(CH_2)_nN(R_{31})(CO(R_{33}))$, $(CH_2)_nN(R_{31})(SO_2(R_{33}))$, or where $R_{20}$ and $R_{21}$, or $R_{21}$ and $R_{22}$, or $R_{22}$ and $R_{23}$ are taken together to form a five or six-membered saturated or unsaturated ring containing 0 or 1 oxygen, nitrogen or sulfur, where the unsaturated ring may be optionally substituted with 1, 2 or 3, $C_1$-$C_6$ alkyl, $C_1$-$C_6$ alkoxy, —OH, —$CH_2OH$, —$(CH_2)_n$—$N(R_{31})(R_{32})$, —$C_3$-$C_8$ cycloalkyl, —$CF_3$, -halo, $CO_2(R_{31})$, —$CON(R_{31})(R_{32})$, —$CO(R_{31})$, —$(CH_2)_nN(R_{31})$ $(CO(R_{33}))$, —$(CH_2)_nN(R_{31})(SO_2$ $(R_{33}))$, —CN, —$CH_2$or —$CH(CF_3)_2$, or phenyl and the saturated ring may be optionally substituted with 1, 2 or 3, —$C_1$-$C_6$ alkyl, —$C_1$-$C_6$ alkoxy, —OH, —$CH_2OH$ or —$(CH_2)_n$—$N(R_{31})(R_{32})$ or one oxo (═O);

where n is 0-3 and $R_{31}$, $R_{32}$ and $R_{33}$ are the same or different and are selected from
—H,
$C_1$-$C_6$ alkyl,
phenyl optionally substituted with 1, 2 or 3-halo, $C_1$-$C_6$ alkyl, $C_1$-$C_6$ alkoxy, —$CF_3$, —OH or —CN,
or where $R_{31}$ and $R_{32}$ taken together with the attached nitrogen to form a ring selected from -pyrrolidinyl, -piperidinyl, -4-morpholinyl, -4-thiomorpholinyl, -4-piperazinyl, -4-(1-$C_1$-$C_6$alkyl)piperazinyl, or a member selected from:

1-cyclohexenyl, 2-pyrimidinyl, 4-pyrimidinyl, 5-pyrimidinyl, 2-imidazolyl, 4-imidazolyl, 2-benzothiazolyl, 2-benzoxazolyl, 2-benzimidazolyl, 2-oxazolyl, 4-oxazolyl, 2-thiazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 1-methylimidazol-2-yl, quinoxalin-2-yl, piperon-5-yl, 4,7-dichlorobenzoxazol-2-yl, 4,6-dimethylpyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazol[1,2-a]pyridin-2-yl, 1-H-inden-3-yl, 1-H-2-methyl-inden-2-yl, 3,4-dihydronaphth-1-yl, S-4-isopropenylcyclohexen-1-yl or 4-dihydronaphth-2-yl;

where $R_{53}$ is selected from —H, $C_1$-$C_6$alkyl, $C_3$-$C_6$cycloalkyl, phenyl (optionally substituted with 1,2, or 3-halo, $C_1$-$C_6$ alkyl, $C_1$-$C_6$ alkoxy, —$CF_3$, —OH, —CN), or a five or six-membered unsaturated ring containing 0 or 1 oxygen, nitrogen or sulfur, where the unsaturated ring may be optionally substituted with —H, $C_1$-$C_6$ alkyl, $C_1$-$C_6$ alkoxy, —OH, —$CH_2OH$, or —$(CH_2)_n$—$N(R_{31})(R_{32})$;

where $R_{54}$ and $R_{55}$ being the same or different are selected from —H, $C_1$-$C_6$ alkyl, allyl, or phenyl (optionally substituted with 1, 2 or 3-halo, $C_1$-$C_6$ alkyl, $C_1$-$C_6$ alkoxy or —$CF_3$), or taken together with the attached nitrogen to form a ring selected from -pyrrolidinyl, -piperidinyl, -4-morpholinyl, -4-thiomorpholinyl, -4-piperazinyl, -4-(1-$C_1$-$C_6$alkyl) piperazinyl;

$R_{41}$ and $R_{42}$, being the same or different, are selected from —H and $C_1$-$C_4$ alkyl;

$R_{12}$ is selected from —H, $C_1$-$C_6$ alkyl, —$C_3$-$C_6$ cycloalkyl, —CN, —$C(O)NH_2$, —$C(O)N(C_1$-$C_6$alkyl)($C_1$-$C_6$alkyl), —$CO_2H$, —$CO_2(C_1$-$C_6$alkyl), —$CH_2OH$, —$CH_2NH_2$ or —$CF_3$;

$R_{13}$ is selected from —H, $C_1$-$C_6$ alkyl or —$CF_3$;
Y is selected from —S—, —S(O)—, —$S(O)_2$, or —O—;
$R_4$ is —OH;
$R_5$ is selected from —H, —$C_2H_4OH$, —$C_2H_4$—O-TBDMS, halo, —$C_3$-$C_6$ cycloalkyl, $C_1$-$C_3$ alkoxy, —$CH_2CH_2Cl$ or $C_1$-$C_4$ alkyl, with the proviso that $R_5$ is not isobutyl;

or, when $R_6$ is hydroxyl, $R_4$ and $R_5$ are taken together to form a five or six-memebered saturated or unsaturated ring which together with the pyrimidine ring form the group consisting of 7H-pyrrolo[2,3-d]pyrimidine, 5,6-dihydro-7H-pyrrolo[2,3-d]pyrimidine, furo[2,3-d]pyrimidine, 5,6-dihydro-furo[2,3-d]pyrimidine, thieno[2,3-d]pyrimidine, 5,6-dihydro-thieno[2,3-d]pyrimidine, 1H-pyrazolo[3,4-d]pyrimidine, 1H-purine, pyrimido[4,5-d]pyrimidine, pteridine, pyrido[2,3-d]pyrimidine, or quinazoline, where the unsaturated ring may be optionally substituted with 1, 2 or 3, $C_1$-$C_6$ alkyl $C_1$-$C_6$ alkoxy, —OH, —$CH_2OH$, or —$(CH_2)n$—$N(R_{31})(R_{32})$, —$C_3$-$C_8$ cycloalkyl, —$CF_3$, -halo, —$CO_2(R_{31})$, —$CON(R_{31})(R_{32})$, —$CO(R_{31})$, —$(CH_2)_nN$ $(R_{31})(CO(R_{33}))$, —$(CH_2)_nN(R_{31})(SO_2(R_{33}))$, and the saturated ring may be optionally substituted with 1, 2 or 3, —$C_1$-$C_6$ alkyl, $C_1$-$C_6$ alkoxy, —OH, —$CH_2OH$, or —$(CH_2)_nN(R_{31})(R_{32})$ or one oxo (=O); and $R_6$ is selected from —H, —OH, halo, —CN, —$CF_3$, —$CO_2(R_{61})$, —$C(O)R_{61}$ or —$C(O)N(R_{61})(R_{62})$ where $R_{61}$ and $R_{62}$ are the same or different and are selected from

—H, $C_1$-$C_6$ alkyl, phenyl optionally substituted with 1, 2 or 3-halo, $C_1$-$C_6$ alkyl, $C_1$-$C_6$ alkoxy, —$CF_3$, —OH, —CN, or where $R_{61}$ and $R_{62}$ taken together with the attached nitrogen to form a ring selected from -pyrrolidinyl, -piperidinyl, -4-morpholinyl, -4-thiomorpholinyl, -4-piperazinyl, or -4-($C_1$-$C_6$ alkyl)piperazinyl; or pharmaceutically acceptable salts, hydrates, N-oxides and solvates thereof.

A preferred embodiment is pyrimidine-thioalkyl and alkylether, where $R_4$ is —OH; and $R_6$ is selected from —H, halo, —CN, —$CF_3$, —$CO_2$ ($R_{16}$), —$C(O)R_{61}$ or —$C(O)N(R_{61})(R_{62})$, preferably $CF_3$.

A preferred embodiment are compounds of Formula XVI where s is 0 or 1, and Y is —S— or O; more preferably Y is —S—.

Preferred are pyrimidine derivatives of the structures

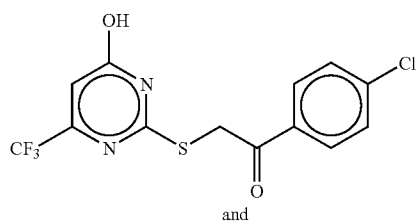

XVIA and

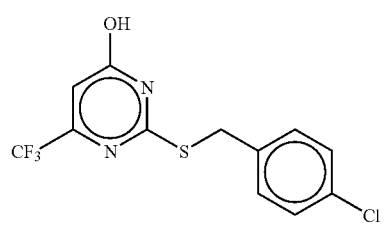

XVIB which may be prepared as disclosed in WO 96/35678.

Another embodiment of the method of the invention includes use of aP2 inhibitors which are pyridazinone derivatives. French Patent No. 2,647,676 discloses compounds which have activity as aP2 inhibitors and thus suitable for use herein which have the structures

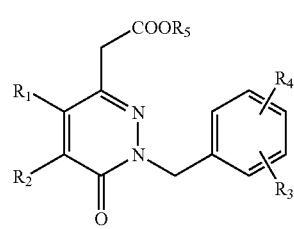

XVIIA

-continued

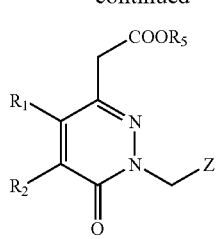

XVIIB where $R_1$ and $R_2$ are H, alkyl, aryl or arylalkyl, where the alkyl can include as substituents halogen, $CF_3$, $CH_3O$, $CH_3S$, $NO_2$, or $R_1$ and $R_2$ with the carbons to which they are attached can form methylenedioxy, or $R_1$ and $R_2$ can form a $C_3$-$C_7$ non-aromatic ring, or a heterocycle which can be pyridine, pyrazine, pyrimidine, pyridazine, indol, or pyrazole, or an oxygen containing heterocycle which can be pyran or furan, or a sulfur containing heterocycle which can be thiopyran, or thiophene; the heterocycles being optionally substituted with halogen or alkyl, $R_3$ and $R_4$ are H, alkyl, halogen, $CF_3$, $CH_3O$, $CH_3S$ or $NO_2$ or $R_3$ and $R_4$ with the carbons to which they are attached can form a methylenedioxy group, $R_5$ is H, and Z is a heterocycle which can be pyridine, thiazole, benzothiazole, benzimidazole or quinoline, which Z group can optionally be substituted with halogen or alkyl.

The preferred pyridazinone derivative is

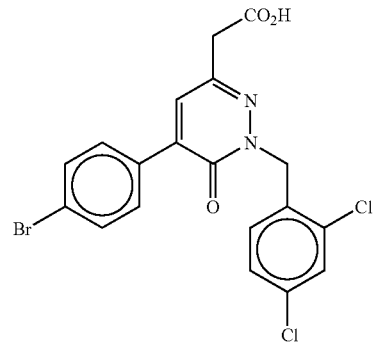

which may be prepared as disclosed in French Patent No. 2,647,676.

Preferred aP2 inhibitors for use herein will include an oxazole ring.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 12 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, acyl, heteroaryl, heteroaryloxy, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

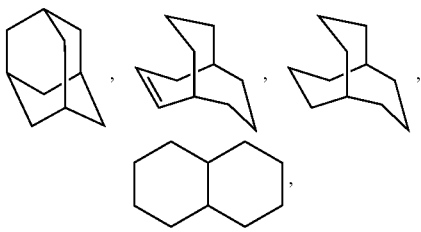

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio.

Unless otherwise indicated the term "aryl" or "Ar" as employed herein alone or as part of another group refers to monocyclic and bicyclic aromatic groups containing 6 to 10 carbons in the ring portion (such as phenyl or naphthyl) and may optionally include one to three additional rings fused to Ar (such as aryl, cycloalkyl, heteroaryl or cycloheteroalkyl rings) and may be optionally substituted through available carbon atoms with 1, 2, 3 or 4 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl.

Unless otherwise indicated the term "aralkyl", "arylalkyl" or "aryllower alkyl" as used herein alone or as part of another group refers to alkyl groups as discussed above having an aryl substituent, such as benzyl or phenethyl, or naphthylpropyl, or an aryl as defined above.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)$. (where p is 1, 2 or 3), such as

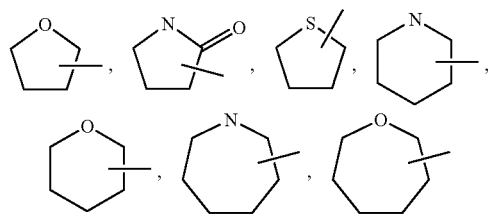

and the like. The above groups may include 1 to 3 substituents such as any of the substituents for alkyl or aryl as defined above. In addition, any of the above rings can be fused to 1 or 2 cycloalkyl, aryl, heteroaryl or cycloheteroalkyl rings.

Unless otherwise indicated, the term "heteroaryl" (also referred to as heteroaryl) as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), linked through a carbon atom or a heteroatom, where possible, optionally via the linker $(CH_2)_p$ (which is defined above), such as

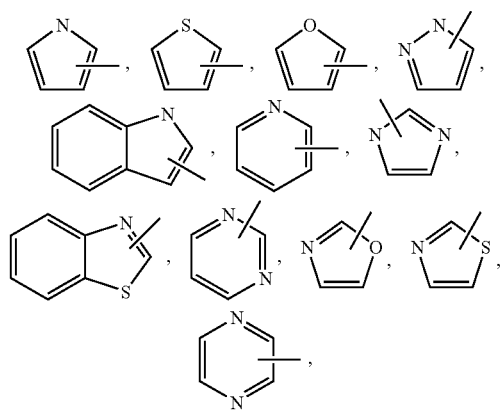

and the like.

The heteroaryl groups including the above groups may optionally include 1 to 4 substituents such as any of the substituents listed for aryl. In addition, any of the above rings can be fused to a cycloalkyl, aryl, heteroaryl or cycloheteroalkyl ring.

The term "prodrug esters" as employed herein includes prodrug esters which are known in the art for both phosphorus and carboxylic acids such as similar carboxylic acid esters such as methyl, ethyl benzyl and the like. Other examples include the following groups: (1-alkanoyloxy) alkyl such as,

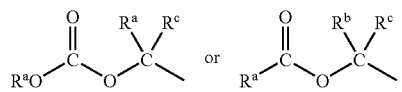

wherein $R^a$, $R^b$ and $R^c$ are H, alkyl, aryl or aryl-alkyl; however $R^aO$ cannot be HO. Examples of such prodrug esters include

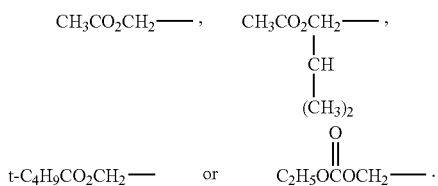

Other examples of suitable prodrug esters include

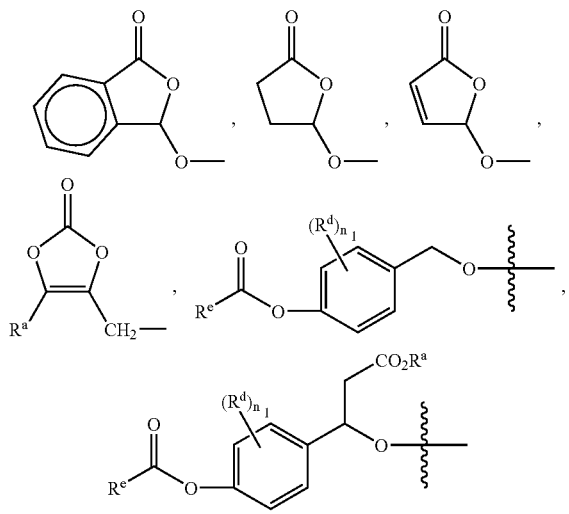

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2; or

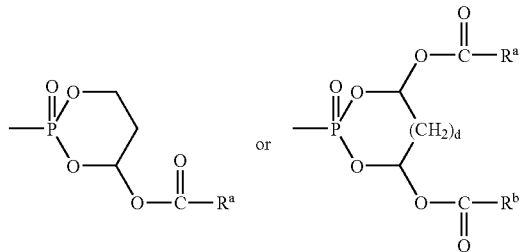

(d is 0 to 3)

Where the aP2 inhibitor is in acid form it may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, ethylenediamine, t-butylamine, t-octylamine, dehydroabietylamine.

Where desired, the aP2 inhibitor may be used in combination with another antiatherosclerotic agent which may be administered orally in the same dosage form in accordance with the invention, a separate oral dosage form or by injection.

It is believed that the use of the aP2 inhibitor in combination with another antiatherosclerotic agent produces antiatherosclerotic results greater than that possible from each of these medicaments alone and greater than the combined additive antiatherosclerotic effects produced by these medicaments.

The other antiatherosclerotic agent employed in the methods of the invention include MTP inhibitors disclosed in U.S. Pat. Nos. 5,595,872, 5,739,135, 5,712,279, 5,760,246, 5,827,875, 5,885,983 and U.S. application Ser. No. 09/175, 180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712, 279, and U.S. Pat. No. 5,760,246.

Thus, preferred compounds in U.S. Pat. Nos. 5,739,135 and 5,712,279 for use herein are compounds of the structure

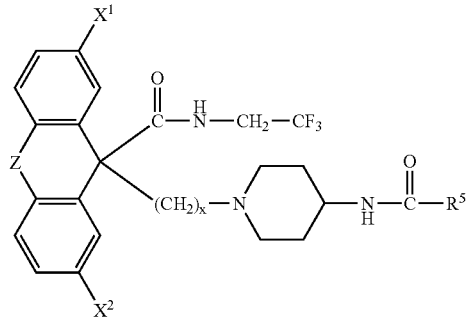

where Z is a bond;
$X^1$ and $X^2$ are H;
$R^5$ is aryl such as phenyl substituted with
(1) aryl such as phenyl,

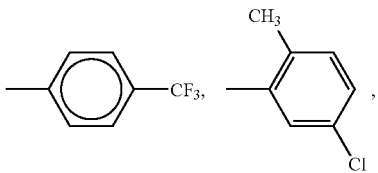

(2) heteroaryl such as

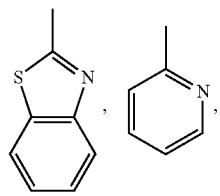

(3) halo such as Cl
$R^5$ is heteroaryl such as

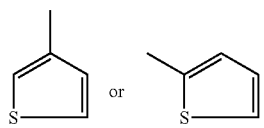

substituted with (1) aroyl such as

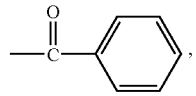

(2) arylthio such as

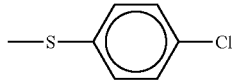

wherein the $R^5$ substituent is preferably in the position adjacent to the carbon linked to

$(CH_2)_x$ is $—(CH_2)_4—$ or

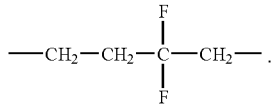

Most preferred is

9-[4-[4-[[2-(2,2,2-Trifluoroethoxy)benzoyl]amino]-1-piperidinyl]butyl]-N-(2,2,2-trifluoroethyl)-9H-fluorene-9-carboxamide

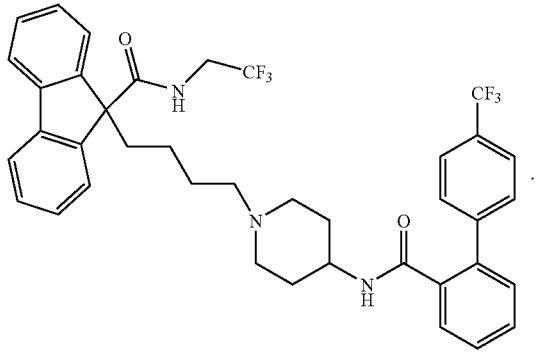

Preferred compounds in U.S. Pat. No. 5,760,246 for use herein are MTP inhibitor compounds which have the formula

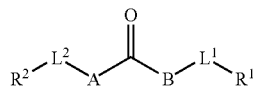

wherein A is NH,

B is

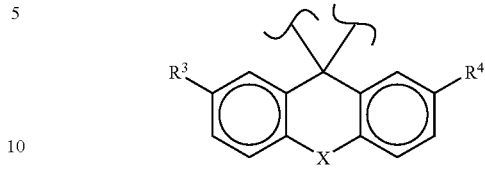

X is a bond, oxygen or sulfur; $R^3$ and $R^4$ are independently H or F.

Preferred $R^1$ groups are aryl, preferably phenyl, heteroaryl, preferably imidazoyl or pyridyl (preferably substituted with one of the preferred $R^1$ substituents: arylcarbonylamino, heteroarylcarbonyl-amino, cycloalkylcarbonylamino, alkoxycarbonylamino, alkylsulfonylamino, arylsulfonylamino, heteroaryl-sulfonylamino), $PO(OAlkyl)_2$, heteroarylthio, benzthiazole-2-thio, imidazole-2-thio, alkyl, or alkenyl, cycloalkyl such as cyclohexyl, or 1,3-dioxan-2-yl.

Preferred $R^2$ groups are alkyl, polyfluoroalkyl (such as 1,1,1-trifluoroethyl), alkenyl, aryl or heteroaryl (preferably substituted with one of the preferred $R^1$ substituents above), or $PO(OAlkyl)_2$.

If $R^2$ is alkyl, 1,1,1-trifluoroethyl, or alkenyl, it is preferred that $R^1$ is other than alkyl or alkenyl.

It is preferred that $L^1$ contains 1 to 5 atoms in the linear chain and $L^2$ is a bond or lower alkylene.

Most preferred is

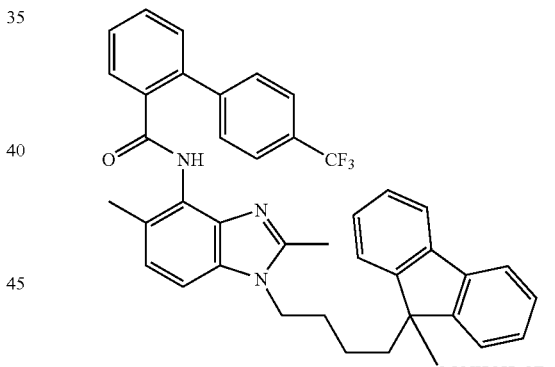

The other antiatherosclerotic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171, with pravastatin, lovastatin or simvastatin being preferred. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pyrazole analogs of mevalonolactone derivatives as disclosed in U.S. Pat. No. 4,613,610, indene analogs of mevalonolactone derivatives as disclosed in PCT application WO 86/03488, 6-(2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, as well as other known HMG CoA reductase inhibitors.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinylmethyl)phosphonates as well as other squalene synthetase inhibitors as disclosed in U.S. Pat. Nos. 4,871,721 and 4,924,024.

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June 1987, Dept. Med. Chem. U of Utah, abstract, Table of Contents, pp 16, 17, 40-43, 48-51, Summary.

Preferred are pravastatin, lovastatin, simvastatin, atorvastatin, fluvastatin and cerivastatin.

All of the above U.S. applications are incorporated herein by reference.

Other cholesterol lowering drugs suitable for use herein include, but are not limited to, antihyperlipoproteinemic agents such as fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred bile acid sequestrants such as cholestyramine, colestipol and DEAE-Sephadex (Secholex®, Polidexide®), as well as clofibrate, lipostabil (Rhone-Poulenc), Eisal E-5050 (an N-substituted ethanolamine derivatives, imanixii (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035. American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives such as disclosed in U.S. Pat. No. 4,759,923, quaternary amine poly(diallyldimethylarmonium chloride) and ionenes such as disclosed in U.S. Pat. No. 4,027,009, and other known serum cholesterol lowering agents.

The above-mentioned U.S. patents are incorporated herein by reference.

The other antiatherosclerotic agent may also be a PPAR α/γ dual agonist such as disclosed by Murakami et al, "A Novel Insulin Sensitizer Acts As a Coligand for Peroxisome Proliferator—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998).

The other antiatherosclerotic agent may be an ACAT inhibitor such as disclosed in, "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62.

The other antiatherosclerotic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties, Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

The aP2 inhibitor will be employed in a weight ratio to the other antiatherosclerotic agent (where present), in accordance with the present invention, within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the other antiatherosclerotic agents will be as disclosed in the various patents and applications discussed above.

The dosages and formulations for the other aniatherosclerotic agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 100 mg/kg and preferably from about 0.1 mg/kg to about 75 mg/kg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For parenteral administration, the MTP inhibitor will be employed in an amount within the range of from about 0.005 mg/kg to about 10 mg/kg and preferably from about 0.005 mg/kg to about 8 mg/kg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The aP2 inhibitor and other antiatherosclerotic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

Tablets of various sizes can be prepared, e.g., of about 2 to 2000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

The formulations as described above will be administered for a prolonged period, that is, for as long as the atherosclerotic condition exists. Sustained release forms of such formulations which may provide such amounts biweekly, weekly, monthly and the like, may also be employed.

In carrying out the method of the invention, a pharmaceutical composition will be employed containing at least one aP2 inhibitor with or without an antiatherosclerotic agent in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 50 and 2,000 mg per day, which can be administered in a single dose or in the form of individual doses from 1-4 times per day.

A typical capsule for oral administration contains aP2 inhibitor (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of aP2 inhibitor into a vial, aseptically freeze-drying and sealing. For use, the contents of the vial are mixed with 2 mL of physiological saline, to produce an injectable preparation.

Compounds sufficiently satisfying the structural criteria described above may be determined by use of an in vitro assay system which measures the potentiation of inhibition of aP2 by displacement of a fluorescent substrate from aP2 by the inhibitor. Inhibition constants (Ki values) for the inhibitors may be determined by the method described below:

Production of purified recombinant human aP2 protein. Recombinant human aP2 protein is produced by standard recombinant DNA technology. In the typical case, aP2 is produced by heterologous expression in *E. coli* strain BL21 (D53) transformed with pETlla vector containing the full length human aP2 cDNA (Baxa, C. A., Sha, R. S., Buelt, M. K., Smith, A. J., Matarese, V., Chinander, L. L., Boundy, K. L., and Bernlohr, D. A. (1989). Human adipocyte lipid-binding protein: purification of the protein and cloning of its complementary DNA. Biochemistry 28: 8683-8690 and Xu, Z., Buelt, M. K.,. Banaszak, L. J., and Bernlohr, D. A. (1991). Expression, purification and crystallization of the adipocyte lipid binding protein. J. Biol. Chem. 266: 14367-14370). Purification of aP2 from *E. coli* is conducted as described by Xu, yielding essentially homogeneous aP2 protein with molecular weight ~14600 daltons and free of endogenous fatty acids. The purified aP2 is capable of binding-up to one mole of free fatty acid per mole protein. The binding and structural properties of recombinant aP2 protein were previously shown to be identical to aP2 protein isolated from adipose tissue.

In vitro assay of aP2 inhibitors. Inhibitors of aP2 are evaluated in a homogeneous fluorescent-based competition assay using recombinant aP2 protein and 1,8-anilino-naphthalene-sulfonic acid (1,8-ANS) as assay substrate. This competition assay was adapted from generalized procedures described previously (Kane, C. D. and Bernlohr, D. A. (1996). A simple assay for intracellular lipid-binding proteins using displacement of 1-anilino-8-sulfonic acid. (1996) Anal. Biochem. 233: 197-204 and Kurian E., Kirk, W. R. and Prendergast, F. G. (1996) Affinity of fatty acid for r-rat intestinal fatty acid binding protein. Biochemistry, 35, 3865-3874). The method relies on the increase in fluorescence quantum yield of 1,8-ANS upon binding to the fatty acid binding site of aP2. The assay is run using appropriate concentrations of inhibitor, 1,8-ANS, and aP2 protein, in order to calculate the inhibitor binding constant (Ki) for compounds being evaluated. The Ki calculation was based on the procedure previously described for calculation of dissociation constants described by Kurian. Lower Ki values indicate higher affinities of compounds binding to aP2.

In the assay as conducted for the inhibitors described herein, a series of aliquots of aP2 (5 μM) in solution in 10 mM potassium phosphate buffer (pH 7.0) are mixed with an equimolar concentration of test compound, followed by the addition of a series of increasing concentrations of 1,8-ANS (from 0 to 5 μM). The assay typically is conducted in 96-well plate format with reagents added using robotic instrumentation (Packard Multiprobe 104). The fluorescence value for each test is determined using a Cytofluor-4000 multi-well fluorescence plate reader (Perceptive Biosystems) using excitation wavelength 360 nm and emission wavelength 460 nm, or using other suitable spectrofluorometer. In preparation for the assay, test compounds are initially prepared at 10 mM in dimethylsulfoxide. All subsequent dilutions and assay additions are made in 10 mM potassium phosphate buffer, pH 7.0.

X-ray crystallography of the inhibitor-aP2 complex can be performed by one skilled in the art using contemporary biophysical methodologies and commercial instrumentation. Such crystallographic data can be used to conclusively determine if a compound used in the present invention has embodied the structural requirement necessary for inhibition of aP2. An example of such an X-ray crystallographic determination is presented below:

Crystals of aP2 complexed with the inhibitors were typically grown by the hanging drop method. aP2, at 8.3 mg/ml, was pre-equilibrated with 1-5 mM of the inhibitor in 0.1 M Tris-HCl pH 8.0, 1% w/v DMSO for four hours. 2 μl drops containing equilibrated protein and reservoir solution at a 1:1 ratio were suspended on plastic cover slips and equilibrated against a 1 ml reservoir containing 2.6-3.0 M ammonium sulfate in 0.1 M Tris-HCl pH 8.0. Crystals typically appeared in 2-3 days and reached maximum size within 2 weeks. Data was typically collected on a single flash-frozen crystal (Oxford Cryosystems) using a Rigaku rotating anode and an R-axis II image plate detector of a Bruker multiwire area detector. Diffraction from aP2 crystals was excellent. Diffraction was consistently observed to better than 2.0 Å resolution often to beyond 1.5 Å resolution. Data was processed either with DENZO/SCALEPACK (R-axis II data), or Xengen (Bruker data). XPLOR was used for structure refinement and model building was done using the molecular modeling package CHAIN. After a single round of refinement, examination of the $F_o$-$F_c$ map typically allowed facile building of the inhibitor into aP2 binding cavity. Iterative fitting and refinement were continued until improvement was no longer seen in the electron density map or R-free.

Referring to the accompanying FIGURE which is a computer generated image of a partial X-ray structure of compound XVIA bound to human aP2, the ball and stick figure in light gray is compound XVIA. The Arg106, Arg126, and Tyr128 residues are depicted as ball and stick figures in dark gray. The dark spheres represent a space filling view of the discrete binding pocket comprised of the residues Phe16, Tyr19, Met20, Val23, Val25, Ala33, Phe57, Thr74, Ala75, Asp76, Arg78. The 4-chlorophenyl substituent of compound XVIA is shown bound within this discrete pocket and the hydroxyl group is bound to the Arg-Tyr-Arg residues.

What is claimed is:

1. A method for treating atherosclerosis which comprises administering to a mammalian species in need of treatment a therapeutically effective amount of an aP2 inhibitor, wherein the aP2 inhibitor is
a diaryloxazole derivative having the structure

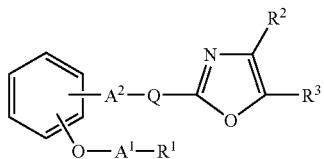

VI wherein R¹ is carboxy or protected carboxy,
R² isaryl,
R³ isaryl,
A¹ is lower alkylene,
A² is bond or lower alkylene and
-Q- is

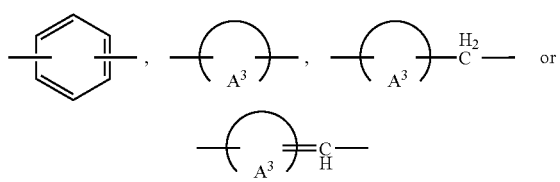

wherein

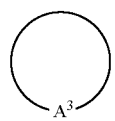

is a lower cycloalkane or a lower cycloalkene, each of which may have suitable substituent(s).

2. A method for treating atherosclerosis which comprises administering to a mammalian species in need of treatment a therapeutically effective amount of an aP2 inhibitor, wherein the aP2 inhibitor has the structure

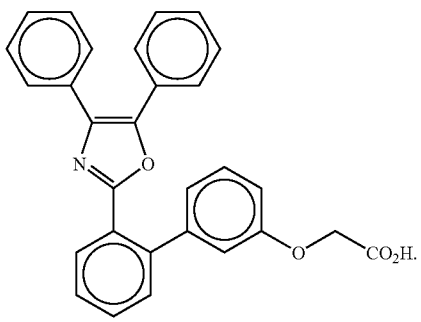

* * * * *

UNITED STATES PATENT AND TRADEMARK OFFICE
CERTIFICATE OF CORRECTION

PATENT NO. : 7,358,254 B2  Page 1 of 1
APPLICATION NO. : 10/872721
DATED : April 15, 2008
INVENTOR(S) : Robl et al.

It is certified that error appears in the above-identified patent and that said Letters Patent is hereby corrected as shown below:

Column 29, Claim 1, line 19, please delete "$R^2$isaryl," and insert -- $R^2$ is aryl, --.

Column 29, Claim 1, line 20, please delete "$R^3$isaryl," and insert -- $R^3$ is aryl, --.

Column 30, Claim 1, line 10, please delete "is a lower cycloalkane or a lower cycloalkene, each of which", and insert -- is a lower ($C_1$-$C_{12}$) cycloalkane or a lower ($C_1$-$C_{12}$) cycloalkene, each of which --.

Signed and Sealed this

Eleventh Day of May, 2010

David J. Kappos
*Director of the United States Patent and Trademark Office*